United States Patent
Bastide et al.

(10) Patent No.: US 11,342,050 B2
(45) Date of Patent: May 24, 2022

(54) MONITORING USERS TO CAPTURE CONTEXTUAL AND ENVIRONMENTAL DATA FOR MANAGING ADVERSE EVENTS

(71) Applicant: International Business Machines Corporation, Armonk, NY (US)

(72) Inventors: Paul R. Bastide, Ashland, MA (US); Fang Lu, Billerica, MA (US); Piyush Madan, Boston, MA (US); Vishrawas Gopalakrishnan, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 145 days.

(21) Appl. No.: 16/585,688

(22) Filed: Sep. 27, 2019

(65) Prior Publication Data

US 2021/0098085 A1 Apr. 1, 2021

(51) Int. Cl.
*G16H 10/20* (2018.01)
*G16H 10/60* (2018.01)
(Continued)

(52) U.S. Cl.
CPC ............ *G16H 10/20* (2018.01); *A61B 5/0004* (2013.01); *A61B 5/0022* (2013.01); *G16H 10/60* (2018.01); *G16H 80/00* (2018.01)

(58) Field of Classification Search
CPC ........ G16H 10/20; G16H 10/60; G16H 80/00; A61B 5/0004; A61B 5/0022
(Continued)

(56) References Cited

U.S. PATENT DOCUMENTS 6,952,695 B1 10/2005 Trinks et al.
2002/0099275 A1* 7/2002 Schmidt ............... A61B 5/0002
128/920
(Continued)

FOREIGN PATENT DOCUMENTS

EP 2755155 A2 7/2014

OTHER PUBLICATIONS

Forouzanfar, R. (2016). Application of mobile phone-based . . . for heart failure management (Order No. 10129880). Available from ProQuest Dissertations and Theses Professional. (1814236482). Retrieved from https://dialog.proquest.com/professional/docview/1814236 (Year: 2016).*

(Continued)

*Primary Examiner* — Christopher L Gilligan
*Assistant Examiner* — Bennett Stephen Erickson
(74) *Attorney, Agent, or Firm* — Edell, Shapiro & Finnan, LLC (57) ABSTRACT

A computer system monitors users to capture contextual and environmental data for managing adverse events of those users. A level of risk for occurrence of an adverse event from performing a medical related activity is determined based on the medical related activity, a medical profile, and a risk profile of the user. The user is monitored to capture environmental and contextual information for the adverse event. The captured information is stored to associate the captured information with the adverse event. In response to occurrence of the adverse event, the user is prompted to provide information pertaining to conditions surrounding the adverse event. The stored information for the adverse event is updated with the user-provided information, and is transmitted to a provider associated with the medical related activity. Embodiments of the present invention further include a method and program product for managing (Continued)

adverse events in substantially the same manner described above.

18 Claims, 4 Drawing Sheets

(51) Int. Cl.
*A61B 5/00* (2006.01)
*G16H 80/00* (2018.01)

(58) Field of Classification Search
USPC .......................................................... 705/2
See application file for complete search history.

(56) References Cited

U.S. PATENT DOCUMENTS

| | | | |
|---|---|---|---|
| 2003/0065241 A1* | 4/2003 | Hohnloser | G16H 10/20 600/1 |
| 2008/0082361 A1* | 4/2008 | Marge | G16H 20/10 705/2 |
| 2009/0006133 A1 | 1/2009 | Weinert et al. | |
| 2011/0112860 A1 | 5/2011 | Kehr | |
| 2014/0344208 A1 | 11/2014 | Ghasemzadeh et al. | |
| 2015/0025329 A1 | 1/2015 | Amarasingham et al. | |
| 2016/0135706 A1* | 5/2016 | Sullivan | A61B 5/7275 600/509 |
| 2017/0032106 A1 | 2/2017 | Abdulahad et al. | |
| 2017/0228745 A1* | 8/2017 | Garcia | G06Q 30/0203 |
| 2018/0166174 A1* | 6/2018 | Lewis | G16H 50/70 |
| 2018/0308569 A1 | 10/2018 | Luellen | |
| 2020/0176118 A1* | 6/2020 | Vemulapalli | A61B 5/14546 |
| 2020/0329982 A1* | 10/2020 | Hengstmann | A61B 5/1118 |

OTHER PUBLICATIONS

H. Cho, "Adverse drug event mining using mobile phone," 2013 International Conference on ICT Convergence (ICTC), Jeju, 2013, pp. 898-899.

A. Mishra, "Towards Automatic Pharmacovigilance: Analysing Patient Reviews and Sentiment on Oncological Drugs," 2015 IEEE International Conference on Data Mining Workshop (ICDMW), Atlantic City, NJ, 2015, pp. 1402-1409.

Y.K. Loke, et al., "Comprehensive evaluations of the adverse effects of drugs: importance of appropriate study selection and data sources", Ther Adv Drug Saf, (2011) 2(2) 59-68, http://taw.sagepub.com, https://www.ncbi.nlm.nih.gov/pmc/articles/PMC4110807/pdf/10.1177_2042098611401129.pdf.

"FDA Adverse Event Reporting System (FAERS): Latest Quarterly Data Files", Aug. 3, 2018, https://www.fda.gov/drugs/questions-and-answers-fdas-adverse-event-reporting-system-faers/fda-adverse-event-reporting-system-faers-latest-quarterly-data-files, 2 pages.

* cited by examiner

MONITORING USERS TO CAPTURE CONTEXTUAL AND ENVIRONMENTAL DATA FOR MANAGING ADVERSE EVENTS

BACKGROUND

1. Technical Field

Present invention embodiments relate to drug safety, and more specifically, to monitoring users to capture contextual and environmental data for managing adverse events of those users.

2. Discussion of the Related Art

Drug safety, also known as pharmacovigilance, refers to the pharmacological science that relates to the collection, detection, assessment, monitoring, and prevention of adverse effects with pharmaceutical products. Adverse events can include any undesired and/or harmful effects resulting at least partially due to administration of pharmaceutical products. Data relating to adverse events can be analyzed in order to understand the underlying causes of events. However, data that could be pertinent to an adverse event may not be collected for a variety of reasons, such as a patient not remembering, or failing to understand the importance of, certain details surrounding an adverse event.

SUMMARY

According to one embodiment of the present invention, a computer system manages adverse events of users by monitoring the users to capture contextual and environmental data. A level of risk for occurrence of an adverse event from performing a medical related activity is determined, wherein the level of risk is based on the medical related activity, a medical profile of a user, and a risk profile of the user. The user is monitored to capture environmental and contextual information for the adverse event, wherein frequency of the monitoring is based on the determined level of risk. The captured information is stored to associate the captured information with the adverse event. In response to occurrence of the adverse event from performance of the medical related activity, the user is prompted to provide information pertaining to conditions occurring prior to the adverse event. The stored information for the adverse event is updated with the information provided by the user. The updated information is transmitted to a provider associated with the medical related activity. Embodiments of the present invention further include a method and program product for managing adverse events of users by monitoring the users to capture contextual and environmental data in substantially the same manner described above.

BRIEF DESCRIPTION OF THE DRAWINGS

Generally, like reference numerals in the various figures are utilized to designate like components.

DETAILED DESCRIPTION

Present invention embodiments relate to drug safety, and more specifically, to monitoring users to capture contextual and environmental data for managing adverse events of those users. Adverse events may refer to any undesired and/or harmful effects caused by medication or other medical interventions, such as surgery. As such, adverse events may include side effects of medications, drug interactions, and other medical errors, such as incorrectly-prescribed medications or even incorrect dosages of correctly-prescribed medications.

Data relating to adverse events can be collected in order to identify and prevent unintended effects of medications. In many countries, adverse events are required by law to be reported, researched in clinical trials, and included in information that accompanies medical devices and drugs for sale to the public. Moreover, investigators are often obligated to report adverse events in clinical report studies. Data relating to adverse events can be used to prevent or mitigate future adverse events. For example, analysis of adverse event data may reveal a previously-unknown drug interaction, which could be easily prevented by prescribing a patient a different medication.

However, it may be difficult to collect data that is relevant to managing adverse events. In particular, patients may not fully recall or appreciate details relating to the context and environment of an adverse event. For example, current weather conditions may be relevant to a patient's skin condition, but the patient may be unaware that weather is a relevant factor. Similarly, a patient may not remember to administer a dosage of a medication whose omission can lead to an adverse event. Present invention embodiments employ techniques to identify and collect contextual and environmental data relating to an adverse event. For example, present invention embodiments may collect environmental and contextual data surrounding an adverse event, such as time, location, weather conditions, characteristics of administration of medications, user characteristics, vital signs of the user, and the like. Once identified and captured, the environmental and contextual data can be used to manage adverse events by warning a user and/or other users of the risk of adverse events occurring. Moreover, by providing investigators with relevant data, a better understanding of adverse events can be achieved. Thus, present invention embodiments enable adverse events to be managed in order to prevent or mitigate future adverse events, thereby increasing the overall well-being of patients while reducing health care expenses. Additionally, present invention embodiments collect data relating to adverse events that would otherwise not be collected, thereby enabling adverse events to be detected and studied where such events might previously go undetected.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but does not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Figure 1:
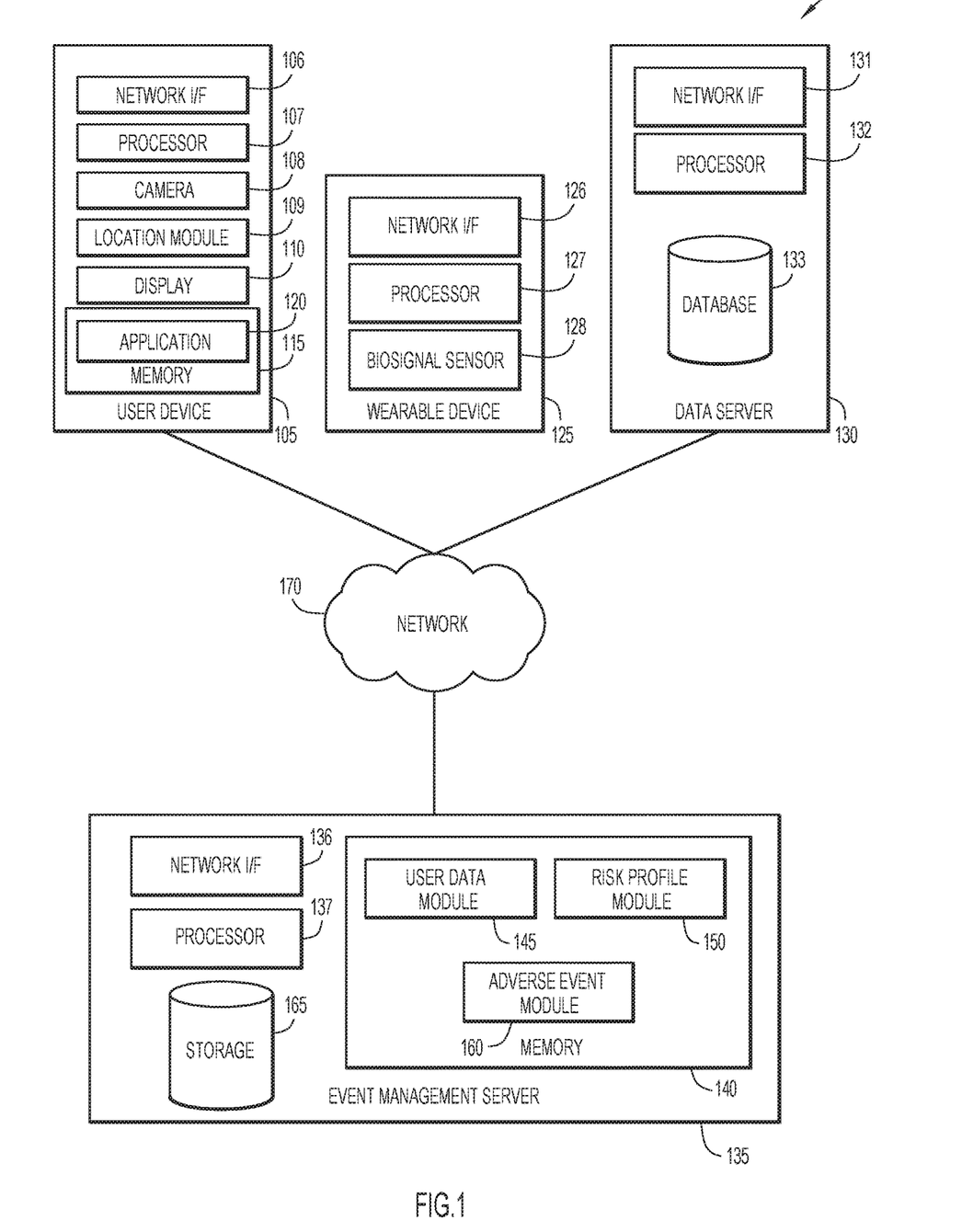
FIG. 1 is a block diagram depicting a computing environment for monitoring users to manage adverse events in accordance with an embodiment of the present invention.

Present invention embodiments will now be described in detail with reference to the Figures. FIG. 1 is a block diagram depicting a computing environment 100 for managing adverse events in accordance with an embodiment of the present invention. As depicted, computing environment 100 includes a user device 105, a wearable device 125, a data server 130, an event management server 135, and a network 170. It is to be understood that the functional division among components of computing environment 100 have been chosen for purposes of explaining present invention embodiments and is not to be construed as a limiting example.

User device 105 includes a network interface (I/F) 106, at least one processor 107, a camera 108, a location module 109, a display 110, and memory 115. Memory 115 may include application 120. User device 105 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 106 enables components of user device 105 to send and receive data over a network, such as network 170. User device 105 may include internal and external hardware components, as depicted and described in further detail with respect to FIG. 4.

Camera 108 may include any conventional or other device capable of capturing still images and/or video. In various embodiments in which user device 105 is a smartphone, tablet, etc., camera 108 may be a front-facing camera or a rear-facing camera. A user of user device 105 may use camera 108 to capture environmental and contextual data associated with adverse events, such as photos and/or videos of the user's person, photos and/or videos of the environment around the user (e.g., photos of the user's location that capture weather or other phenomena), and the like.

Location module 109 may include any device capable of determining the location of user device 105. Location may include one or more of address, latitude, longitude, and elevation. In one embodiment, location module 109 receives signals from a global positioning system in order to determine location. In another embodiment, location module 109 uses ground-based or other triangulation techniques to determine location. Location module 109 may share the location of user device 105 with event management server 135.

Display 110 may include any electronic device capable of presenting information in a visual form. For example, display 110 may be a liquid crystal display (LCD), a cathode ray tube (CRT) display, a light-emitting diode (LED) display, an electronic ink display, and the like. Information relating to adverse events, including the capture of environmental and contextual information associated with adverse events, may be displayed to a user of user device 105 via display 110.

Application 120 may include one or more modules or units to perform various functions of present invention embodiments described below. Application 120 may be implemented by any combination of any quantity of software and/or hardware modules or units, and may reside within memory 115 of user device 105 for execution by a processor, such as processor 107.

Application 120 may enable a user of user device 105 to manage adverse events and to provide information related to adverse events. In some embodiments, a user of user device 105 may provide information, via application 120, to event management server 135 and its modules, including environmental and contextual information relating to an adverse event. For example, a user may be prompted via application 120 to provide feedback such as a user's current physical and mental sensations, such as mood, feelings, sensations, qualia, and the like. In some embodiments, a user may interact with application 120 to complete quizzes or questionnaires that include questions and answers designed to elicit information relating to the user's cognitive load, feelings, sentiment, etc.

Wearable device 125 includes a network interface 126, at least one processor 127, and at least one biosignal sensor 128. In various embodiments of the present invention, wearable device 125 may include any computing device that can be worn on, or otherwise associated with, a user's person, such as a smart watch, a heart rate monitor, apparel that includes electronic textiles, and the like. Wearable device 125 may be placed on a user's person in a location conducive to the collection of biosignals, which include any measurable electrical or non-electrical signal produced by a user's body. Wearable device 125 may include internal and external hardware components, as depicted and described in further detail with respect to FIG. 4.

Biosignal sensor 128 may collect data corresponding to biosignals produced by a user's body. In various embodiments, biosignal sensor 128 may include any conventional or other transducer of biosignals, including a heart rate monitor, a pulse oximeter, a thermometer, an electrodermal activity sensor, a blood pressure monitor, a blood sugar monitor, and the like. Biosignal sensor 128 may share, via network interface 126, collected data with other devices, including user device 105, data server 130, and/or event management server 135.

Data server 130 includes a network interface 131, at least one processor 132, and at least one database 133. In various embodiments of the present invention, data server 130 may include a laptop computer, a tablet computer, a netbook computer, a personal computer (PC), a desktop computer, a personal digital assistant (PDA), a smart phone, or any programmable electronic device capable of executing computer readable program instructions. Network interface 131 enables components of data server 130 to send and receive data over a network, such as network 170. In general, data server 130 may store data relating to the health care of users, including user biometrics (e.g., age, height, weight, etc.), medications prescribed to users, medical histories of users, and other relevant information. In some embodiments, data server 130 may be associated with a public or private health care organization, or may be associated with a governmental organization, such as a regulatory body. In some embodiments, data server 130 stores electronic health records of one or more users.

Database 133 may include any non-volatile storage media known in the art. For example, database 133 can be implemented with a tape library, optical library, one or more independent hard disk drives, or multiple hard disk drives in a redundant array of independent disks (RAID). Similarly, data on database 133 may conform to any suitable storage architecture known in the art, such as a file, a relational database, an object-oriented database, and/or one or more tables. In some embodiments, database 133 stores data relating to the health care of users, including electronic health records of users, user-provided data, and the like.

Event management server 135 includes a network interface 136, at least one processor 137, memory 140, and storage 165. Memory 140 includes a user data module 145, a risk profile module 150, and an adverse event module 160. In various embodiments of the present invention, event management server 135 may include a laptop computer, a tablet computer, a netbook computer, a personal computer (PC), a desktop computer, a personal digital assistant (PDA), a smart phone, or any programmable electronic device capable of executing computer readable program instructions. Network interface 136 enables components of event management server 135 to send and receive data over a network, such as network 170. In general, event management server 135 and its modules may manage adverse events by identifying and collecting environmental and contextual data surrounding events, identifying the occurrence of adverse events, and notifying users about adverse events. Event management server 135 may include internal and external hardware components, as depicted and described in further detail with respect to FIG. 4.

User data module 145, risk profile module 150, and adverse event module 160 may include one or more modules or units to perform various functions of present invention embodiments described below. User data module 145, risk profile module 150, and adverse event module 160 may be implemented by any combination of any quantity of software and/or hardware modules or units, and may reside within memory 140 of event management server 135 for execution by a processor, such as processor 137.

User data module 145 may obtain data to support the management of adverse events, including data relating to a user's medical activity, medical profile data of users, and risk profile data of users. In some embodiments, user data module 145 obtains information pertaining to a user's health from user device 105 and/or data server 130. User data module 145 may obtain electronic health records of a user that include structured and/or unstructured data. A user's medical profile information may include the user's age, biometric information such as weight, height, etc., medications that a user is prescribed, medical conditions with which a user has been diagnosed, a user's medical history, and the like.

Additionally or alternatively, user data module 145 may obtain data relating to a user's environment, such as environmental conditions of a user's location. For example, user data module 145 may receive an indication of a user's location from location module 109 of user device 105, and may retrieve (e.g., from a third-party website or database) environmental information relating to that location at the time, such as weather conditions (e.g., temperature, humidity, precipitation, wind speed, air pressure, pollen count, ultraviolet (UV) index, air quality index (AQI), and the like).

User data module 145 may obtain data on a prearranged schedule or on an ad hoc basis (e.g., when data becomes available). In some embodiments, user data module 145 obtains data at predetermined intervals that correspond to a user's risk level. For example, if risk profile module 150 determines that a level of risk of a particular user experiencing an adverse event is high, user data module 145 may obtain data relating to that user at a greater frequency. User data module 145 may store obtained data in storage 165 so that the data may be accessible to other modules of event management server 135 and/or other computing devices, such as user device 105 or data server 130. In some embodiments, user data module 145 stores obtained data of users for a predetermined period of time before discarding, overwriting, etc. the obtained data. For example, user data module 145 may store a rolling time window of the last twenty-four hours of data collected from a user. The duration for storing captured data may be predetermined, may be based on a user's level of risk, and/or may be based on the half-life of a medication that is prescribed to a user. In some embodiments, user data module 145 may not collect data from a user unless the user's level of risk of experiencing an adverse event exceeds a predetermined threshold. User data module 145 may periodically prompt a user to log the user's feelings and sentiments via application 120.

Risk profile module 150 may establish risk profiles for users and determine each user's level of risk of experiencing an adverse event. The risk profile may be based on one or more of the newness of medications in the medical profile of a user, characteristics of administration of a medication, prior adverse events experienced by the user, characteristics of the user, and the risk using the medication based on any populations to which the user belongs.

Newness of a medication may refer to how recently a user has begun to administer a medication. For example, if a user has been administering a medication for months or years without an adverse event, that medication is likely to correspond to a low risk; however, if a user has recently added a new medication to the user's health care routine, the new medication may represent a degree of uncertainty and may thus be associated with a higher risk. Risk profile module 150 may calculate a ratio of a user's new medications to old medications. For example, if a user is on many new medications and few or no old medications, the user may be deemed to be at higher risk of an adverse event. Newness of a medication may be determined according to a predetermined threshold; for example, and medication that the user has been administering for over one month, two months, six months, one year, etc., may be considered to be old. Thus, the risk profile of a user may be limited based on the immediacy of initial administration of a medication.

Characteristics of administration of a medication may include, for each medication prescribed or otherwise administered to a user, the dosage of the medication and the schedule of the dosage. For example, a twenty milligram dosage of a particular medication may be administered once a day in the morning. For medications that are administered in an unscheduled manner, a user may provide an indication of when the user has administered the medication. For example, if a user administers a particular medication when the user experiences nausea, before the user ingests a meal containing lactose, etc., the user may indicate to application 120 that the medicine has been administered. In some embodiments, characteristics of administration of a medication may include an identity of who administered the medication (e.g., the user, a parent or guardian, etc.).

Prior adverse events experienced by the user may include any previous adverse events in the user's medical history, along with relevant data in the user's medical history that is contemporaneous with prior adverse events. In particular, medications that were prescribed to a user when the user experienced a prior adverse event may be relevant to a user's current risk profile. For example, if a user previously experienced an allergy in response to administration of a particular drug, the adverse event and drug may be included in the user's risk profile, as administration of a drug in a similar class as the previous drug could potentially trigger another adverse event. Prior adverse events may be based on combinations of medications that produce adverse events. In some embodiments, prior adverse events are based on the time of the initial administration of a medication to a median occurrence of an adverse event; for example, if an adverse event lasts six hours, the median occurrence time occurs at the three-hour mark, and the time duration would span from the time at which the medication is administered to the median occurrence time. In some embodiments, a risk profile may include the amount of time that has elapsed since observation of the previous adverse event. For example, the observation time may be a duration between administration of a medication and observation of an adverse event in response to the medication.

Risk of using the medication based on a user's population may be an assessment of a user's risk based on demographic information of the user. In particular, factors such as age, gender, ethnicity, specific medical history, and combinations thereof and the like may place a user at a greater or lower risk of suffering an adverse event from a particular medication. For example, a male who is over forty-five and has a history of kidney disease may be at higher risk of having an adverse reaction to a particular medication as compared to other populations.

Risk profile module 150 may determine a level of risk for a user based on the user's risk profile. Risk profile module 150 may assign scores to each element of a risk profile, and may compute an overall score (e.g., a sum, an average, a weighted sum, etc.) indicating a user's level of risk of experiencing an adverse event. The user's level of risk may correspond to a qualitative category of risk, such as "unlikely" or "extremely likely," and/or the level of risk may be a quantitative value.

Adverse event module 160 may analyze data collected by user data module 145 to monitor a user's health in order to detect and respond to adverse events. Additionally, adverse event module 160 may transmit collected environmental and contextual data relating to an adverse event to other recipients, such as regulatory bodies, and may alert users who are affected by, or potentially affected by, adverse events.

When a user experiences an adverse event, adverse event module 160 may identify any collected information related to the event and may initiate collection of more additional data. Adverse event module 160 may be notified of an adverse event by a user, who may indicate that he or she has experienced an adverse event via application 120 of user device 105 and/or by wearable device 125. Additionally or alternatively, adverse event module 160 may receive a notification sent from a health care professional indicating that a user has experienced an adverse event. The notification may include details of the adverse event, including symptoms experienced and the time of onset of the adverse event.

In some embodiments, adverse event module 160 detects occurrence of adverse events by monitoring data collected by user data module 145. In particular, adverse event module 160 may analyze biometric information collected from wearable device 125. For example, adverse event module 160 may analyze heart rate information to determine that a user is experiencing atrial fibrillation.

Upon occurrence of an adverse event, adverse event module may prompt the user to provide feedback via application 120. In particular, a user may be prompted to describe their adverse event, including time of onset and physiological characteristics, such as symptoms, pain level, and any other details that the user can provide. A user may also be prompted to provide one or more pictures of portions of the user's body. For example, if a user's adverse event includes a rash on the user's forearm, adverse event module 160 may prompt the user to take a picture of their forearm using camera 108 of user device 105. All feedback collected by the user may be transmitted to event management server 135 for further analysis and dissemination.

Adverse event module 160 may instruct user data module 145 to collect feedback from a user by prompting the user with a questionnaire of open-ended and/or close-ended questions. A questionnaire may be transmitted to application 120 of user device 105 for the user to complete. Based on the user's feedback, adverse event module 160 may determine the user's cognitive load, and any feelings or sentiments relating to the adverse event. For example, the user may indicate any feelings of nausea, sweating, happiness or sadness, and/or other psycho-pharmaceutical indicators. In some embodiments, a user periodically provides feedback regardless of whether the user has or has not experienced an adverse event, and the frequency of prompts for feedback may be adjusted according to the user's risk profile.

Adverse event module 160 may update the stored information for an adverse event with information provided by or collected from a user. The stored information for an adverse event may include information associated with a user that is collected in a particular time period around the adverse event. For example, the information may include all or some of a user's medication administrations within hours, days, etc., of the adverse event, as well as any other collected data, such as the user's biometric information. The updated information may then be transmitted to other recipients, such as a health care provider associated with the medical-related activity that triggered the adverse event. In some embodiments, adverse event module 160 may notify the user that the user has experienced an adverse event. Additionally or alternatively, adverse event module 160 may notify other users who have similar risk profiles as the user that an adverse event has occurred, and may alter monitoring of the other users in order to collect additional data from the users. For example, if a user experiences an adverse event, adverse event module 160 may notify other users whose risk profiles are similar to the user, and may modify the data collection schedule of those users from a daily collection to an hourly collection.

Storage 165 may include any non-volatile storage media known in the art. For example, storage 165 can be implemented with a tape library, optical library, one or more independent hard disk drives, or multiple hard disk drives in a redundant array of independent disks (RAID). Similarly, data stored in storage 165 may conform to any suitable storage architecture known in the art, such as a file, a relational database, an object-oriented database, and/or one or more tables. Storage 165 may store data relating to managing adverse reactions, including environmental and contextual data relating to adverse events, user medical profiles, user risk profiles, and the like.

Network 170 may include a local area network (LAN), a wide area network (WAN) such as the Internet, or a combination of the two, and includes wired, wireless, or fiber optic connections. In general, network 170 can be any combination of connections and protocols known in the art that will support communications between user device 105, wearable device 125, data server 130, and/or event management server 135 via their respective network interfaces in accordance with embodiments of the present invention.

Figure 2:
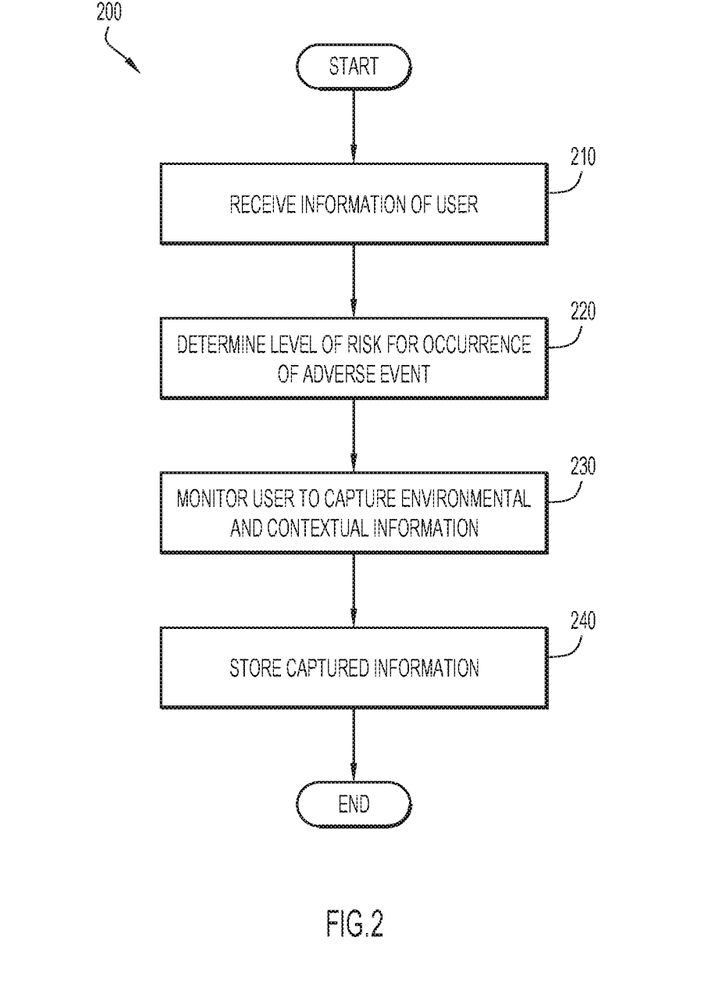
FIG. 2 is a flow chart depicting a method of identifying and capturing contextual and environmental data in accordance with an embodiment of the present invention.

FIG. 2 is a flow chart depicting a method 200 of identifying and capturing contextual and environmental data in accordance with an embodiment of the present invention.

Information of a user is received at operation 210. User data module 145 may obtain information relating to a user, such as the user's electronic health records, to establish a medical profile and risk profile for the user. A user's medical profile information may include the user's age, biometric information such as weight, height, etc., medications that a user is prescribed, medical conditions with which a user has been diagnosed, a user's medical history, and the like. A user's risk profile may be based on one or more of the newness of medications in the medical profile of a user, characteristics of administration of a medication, prior adverse events experienced by the user, characteristics of the user, and the risk using the medication based on any populations to which the user belongs. Information of a user may be received from one or more sources, such as user device 105 and/or data server 130.

A level of risk of occurrence of an adverse event is determined for a user at operation 220. Risk profile module 150 may assess a level of risk of a user based on the user's risk profile. In some embodiments, each element of a user's risk profile may contribute toward a total risk score. For example, the occurrence of prior adverse events may raise a user's risk score, whereas if a user's biometrics indicate that, based on the user's height and weight, the user has a healthy body mass index (BMI) value, then the user's level of risk may be lowered accordingly.

The user is monitored to capture environmental and contextual information at operation 230. Adverse event module 160 may monitor data collected by user data module 145, including user feedback elicited from questionnaires, environmental data based on the user's location, and/or user vital signs captured by biosignal sensor 128. A user may be monitored in response to one or more conditions that are conducive for occurrence of an adverse event. For example, if an adverse event is caused by excessive heat, a user's location may be monitored in order to collect weather data, such as temperature and humidity.

The captured information is stored at operation 240. Captured information may be stored in storage 165 for analysis by modules of event management server 135. When an adverse event occurs, captured information may be made available to other parties, such as a health care provider of the user.

Figure 3:
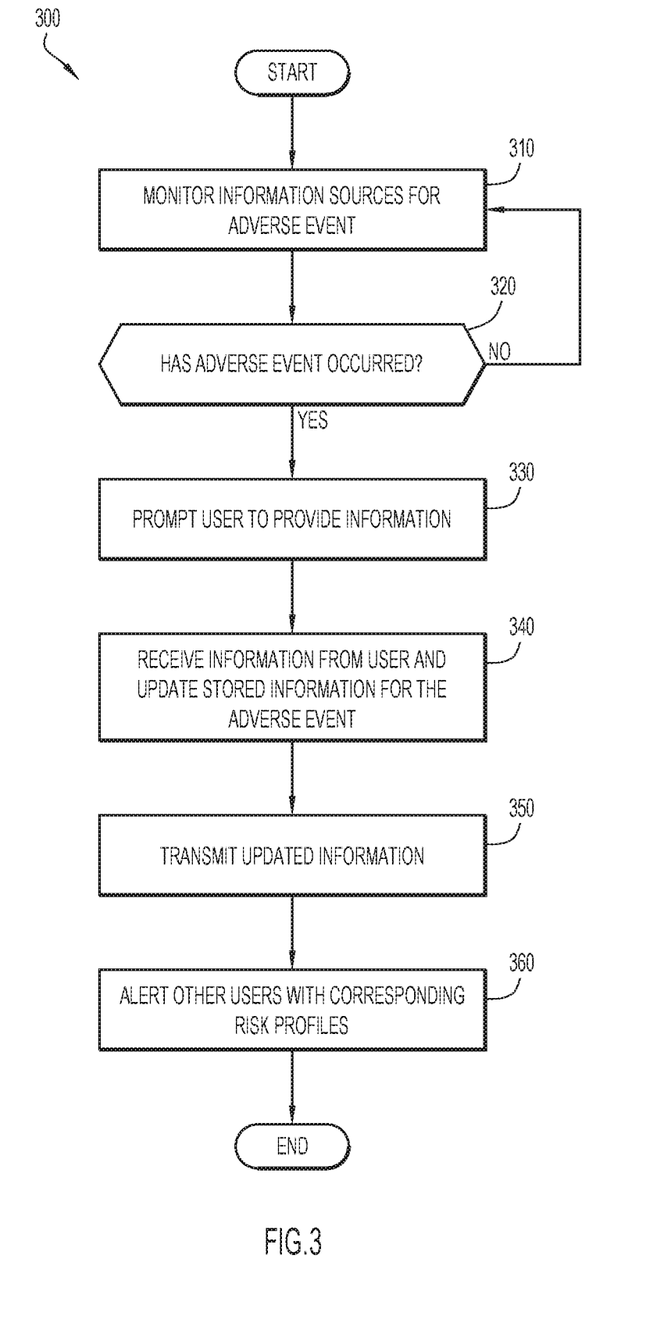
FIG. 3 is a flow chart depicting a method of managing adverse events in accordance with an embodiment of the present invention.

FIG. 3 is a flow chart depicting a method 300 of managing adverse events in accordance with an embodiment of the present invention.

Information sources are monitored for occurrence of an adverse event at operation 310. In particular, adverse event module 160 may receive an indication from a health care professional alerting that a user has experienced an adverse event. An indication that an adverse event has occurred may include a time of onset of the adverse event. Alternatively, adverse event module 160 may monitor user data collected by user data module 145 to identify the occurrence of an adverse event. For example, data relating to a user's vital signs may be analyzed to identify the occurrence of an adverse event. The adverse event may result from performing a particular medical-related activity, such as administration of a medication.

Operation 320 determines whether an adverse event has occurred. If an adverse event has occurred, a user is prompted to provide more information at operation 330. Otherwise, adverse event module 160 continues to monitor for the occurrence of an adverse event at operation 310.

Adverse event module 160 may prompt a user to provide more information that may be relevant to investigating the adverse event. Adverse event module 160 may transmit a questionnaire or other instructions to provide feedback to user device 105 for presentation to the user via application 120. In particular, the user may be prompted via open-ended and/or close-ended questions to describe their feelings and sentiments at the time of the adverse event. A user may be instructed to provide physical documentation of the user's person and/or the user's environment at the time of the adverse event's occurrence. For example, a user may be prompted to take a picture of a physical symptom that the user is experiencing.

Information is received from the user and the stored information for the adverse event is updated accordingly at operation 340. The user-provided information may be used to update other stored information relating to the adverse event, such as information already collected by user data module 145 (e.g., vital sign information, user medical history, etc.).

The updated information is transmitted to one or more parties at operation 350. Adverse event module 160 may transmit the updated information to a provider associated with the medical-related activity, such as a health care provider of the user. Additionally or alternatively, adverse event module 160 may transmit the data to the user for the user's own records, or other user-approved recipients. Adverse event module 160 may alert the user with a notification template related to risk and current adverse events. In particular, the template may be populated with a user's specific risks incurred by the user's medical-related activities based on the contextual and environmental data gathered about the user, along with any details about adverse events experienced by the user.

Other users with corresponding risk profiles are alerted at operation 360. Based on the user's risk profile and the medical-related activity or activities associated with the adverse event, adverse event module 160 may identify other users sharing similar risk profiles and/or administered medications as the user. Thus, other users may be warned of potential causes of adverse events so that the users may avoid the occurrence of, or mitigate the severity of, an adverse event.

Figure 4:
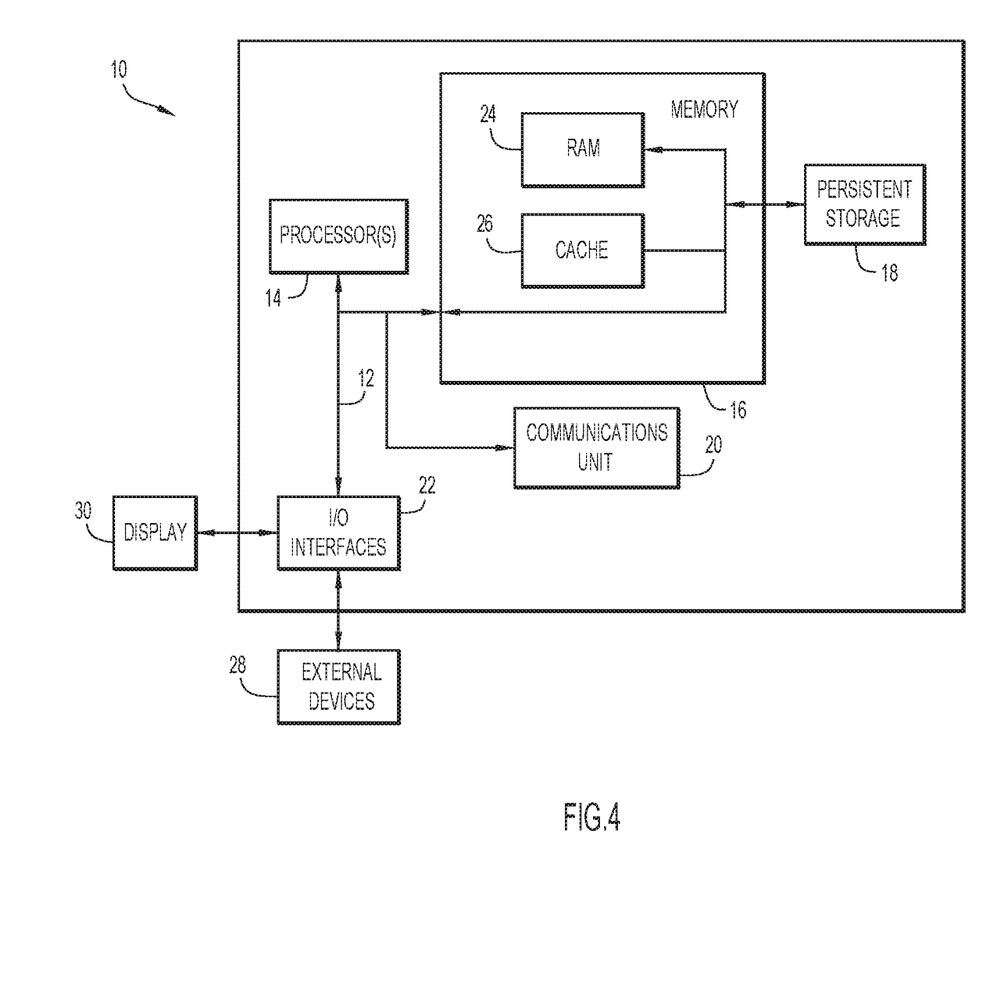
FIG. 4 is a block diagram depicting a computing device in accordance with an embodiment of the present invention.

FIG. 4 is a block diagram depicting components of a computer 10 suitable for executing the methods disclosed herein. Computer 10 may implement user device 105, wearable device 125, data server 130, and/or event management server 135 in accordance with embodiments of the present invention. It should be appreciated that FIG. 4 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to managing adverse events of users using captured contextual and environmental data (e.g., user medical profile data, user risk profile data, captured contextual and environmental data including user feedback data, user biosignal data, etc.) may be stored within any conventional or other data structures (e.g., files, arrays, lists, stacks, queues, records, etc.) and may be stored in any desired storage unit (e.g., database, data or other repositories, queue, etc.). The data transmitted between user device 105, wearable device 125, data server 130, and/or event management server 135 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to managing adverse events of users using captured contextual and environmental data (e.g., user medical profile data, user risk profile data, captured contextual and environmental data including user feedback data, user biosignal data, etc.) may include any information provided to, or generated by, user device 105, wearable device 125, data server 130, and/or event management server 135. Data relating to managing adverse events of users using captured contextual and environmental data may include any desired format and arrangement, and may include any quantity of any types of fields of any size to store any desired data. The data relating to managing adverse events of users using captured contextual and environmental data may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to managing adverse events of users using captured contextual and environmental data), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of implementing embodiments for monitoring users to captured contextual and environmental data for managing adverse events of those users.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., communications software, server software, application 120, user data module 145, risk profile module 150, adverse event module 160, etc.). These systems may include any types of monitors and input devices (e.g., keyboard, mouse, voice recognition, etc.) to enter and/or view information.

It is to be understood that the software (e.g., communications software, server software, application 120, user data module 145, risk profile module 150, adverse event module 160, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., communications software, server software, application 120, user data module 145, risk profile module 150, adverse event module 160, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to managing adverse events of users using captured contextual and environmental data). The database system may be implemented by any number of any conventional or other databases, data stores or storage structures (e.g., files, databases, data structures, data or other repositories, etc.) to store information (e.g., data relating to managing adverse events of users using captured contextual and environmental data). The database system may be included within or coupled to the server and/or client systems. The database systems and/or storage structures may be remote from or local to the computer or other processing systems, and may store any desired data (e.g., data relating to managing adverse events of users using captured contextual and environmental data).

The present invention embodiments may employ any number of any type of user interface (e.g., Graphical User Interface (GUI), command-line, prompt, etc.) for obtaining or providing information (e.g., data relating to managing adverse events of users using captured contextual and environmental data), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for any number of applications in the relevant fields, including, but not limited to, collecting environmental and contextual data relating to users in order to identify, study, prevent, and/or manage a variety of health-related or other events, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for managing and capturing information for a medical related adverse event comprising:

determining, via a processor, a level of risk for occurrence of an adverse event from performing a medical related activity, wherein the level of risk is based on the medical related activity, a medical profile of a user, and a risk profile of the user, and wherein the adverse event includes a side effect of a medication;

monitoring the user, via the processor, to capture environmental and contextual information for the adverse event, wherein frequency of the monitoring is based on the determined level of risk, wherein capturing the environmental and contextual information includes determining, via a location module, a location of the user and transmitting, via the processor, the location to determine weather conditions of the location at a time of the adverse event, and wherein the environmental and contextual information includes biosignal data of the user captured via one or more wearable sensors;

storing, via the processor, the captured information to associate the captured information with the adverse event; and in response to occurrence of the adverse event from performance of the medical related activity:

prompting, via the processor, the user to provide information pertaining to conditions occurring prior to the adverse event, wherein prompting the user further comprises one or more from a group of:

transmitting, at a time of the adverse event, a questionnaire to the user to determine a cognitive load; and transmitting, at the time of the adverse event, requests for information pertaining to user feelings and sentiments;

updating, via the processor, the stored information for the adverse event with the information provided by the user; and transmitting, via the processor, the updated information to a provider associated with the medical related activity.

2. The computer-implemented method of claim 1, wherein the user includes a patient, the medical related activity includes administering medication, and the risk profile is based on one or more from a group of: newness of medications in the medical profile of the user, characteristics of administration of the medication, prior adverse events, characteristics of the user, and risk of using the medication based on populations.

3. The computer-implemented method of claim 2, wherein the prior adverse events are based on one or more from a group of: combinations of medications that produce adverse events, time of initial administration to a median occurrence of an adverse event, and an observation time until occurrence of an adverse event.

4. The computer-implemented method of claim 2, wherein determining the level of risk further comprises:

limiting the risk profile based on immediacy of administration of the medication.

5. The computer-implemented method of claim 1, wherein the environmental and contextual information further includes one or more from a group of: time, and physiological characteristics of the user.

6. The computer-implemented method of claim 1, further including:

alerting one or more other users with corresponding risk profiles and altering monitoring of the other users in response to occurrence of the adverse event.

7. The computer-implemented method of claim 1, wherein monitoring the user further comprises:

monitoring the user in response to one or more conditions conducive for occurrence of the adverse event.

8. The computer-implemented method of claim 1, further comprising:

alerting the user to report a potential adverse event based on one or more from a group of an amount of captured information and an analysis of the captured information indicating occurrence of the potential adverse event.

9. The method of claim 1, further comprising:

alerting the user with a notification template related to risk and current adverse events.

10. The computer-implemented method of claim 1, wherein the processor includes a mobile device.

11. A computer system for managing and capturing information for a medical related adverse event, the computer system comprising:

one or more computer processors;

one or more computer readable storage media;

program instructions stored on the one or more computer readable storage media for execution by at least one of the one or more computer processors, the program instructions comprising instructions to:

determine a level of risk for occurrence of an adverse event from performing a medical related activity, wherein the level of risk is based on the medical related activity, a medical profile of a user, and a risk profile of the user, and wherein the adverse event includes a side effect of a medication;

monitor the user to capture environmental and contextual information for the adverse event, wherein frequency of the monitoring is based on the determined level of risk, wherein capturing the environmental and contextual information includes determining, via a location module, a location of the user and transmitting, via the processor, the location to determine weather conditions of the location at a time of the adverse event, and wherein the environmental and contextual information includes biosignal data of the user captured via one or more wearable sensors;

store the captured information to associate the captured information with the adverse event; and in response to occurrence of the adverse event from performance of the medical related activity:

prompt the user to provide information pertaining to conditions occurring prior to the adverse event, wherein prompting the user further comprises one or more from a group of:

transmitting, at a time of the adverse event, a questionnaire to the user to determine a cognitive load; and transmitting, at the time of the adverse event, requests for information pertaining to user feelings and sentiments;

update the stored information for the adverse event with the information provided by the user; and transmit the updated information to a provider associated with the medical related activity.

12. The computer system of claim 11, wherein the user includes a patient, the medical related activity includes administering medication, and the risk profile is based on one or more from a group of: newness of medications in the medical profile of the user, characteristics of administration of the medication, prior adverse events, characteristics of the user, and risk of using the medication based on populations.

13. The computer system of claim 12, wherein the prior adverse events are based on one or more from a group of: combinations of medications that produce adverse events, time of initial administration to a median occurrence of an adverse event, and an observation time until occurrence of an adverse event.

14. The computer system of claim 11, wherein the environmental and contextual information includes one or more from a group of: time, and physiological characteristics of the user.

15. A computer program product for managing and capturing information for a medical related adverse event, the computer program product comprising one or more computer readable storage media collectively having program instructions embodied therewith, the program instructions executable by a computer to cause the computer to:

determine a level of risk for occurrence of an adverse event from performing a medical related activity, wherein the level of risk is based on the medical related activity, a medical profile of a user, and a risk profile of the user, and wherein the adverse event includes a side effect of a medication;

monitor the user to capture environmental and contextual information for the adverse event, wherein frequency of the monitoring is based on the determined level of risk, wherein capturing the environmental and contextual information includes determining, via a location module, a location of the user and transmitting, via the processor, the location to determine weather conditions of the location at a time of the adverse event, and wherein the environmental and contextual information includes biosignal data of the user captured via one or more wearable sensors;

store the captured information to associate the captured information with the adverse event; and in response to occurrence of the adverse event from performance of the medical related activity:

prompt the user to provide information pertaining to conditions occurring prior to the adverse event, wherein prompting the user further comprises one or more from a group of:

transmitting, at a time of the adverse event, a questionnaire to the user to determine a cognitive load; and transmitting, at the time of the adverse event, requests for information pertaining to user feelings and sentiments;

update the stored information for the adverse event with the information provided by the user; and transmit the updated information to a provider associated with the medical related activity.

16. The computer program product of claim 15, wherein the user includes a patient, the medical related activity includes administering medication, and the risk profile is based on one or more from a group of: newness of medications in the medical profile of the user, characteristics of administration of the medication, prior adverse events, characteristics of the user, and risk of using the medication based on populations.

17. The computer program product of claim 16, wherein the prior adverse events are based on one or more from a group of: combinations of medications that produce adverse events, time of initial administration to a median occurrence of an adverse event, and an observation time until occurrence of an adverse event.

18. The computer program product of claim 15, wherein the environmental and contextual information includes one or more from a group of: time, and physiological characteristics of the user.

\* \* \* \* \*